United States Patent [19]

Lappas et al.

[11] 4,223,153

[45] Sep. 16, 1980

[54] CRYSTALLINE FORMS OF N-2-(6-METHOXY)BENZOTHIAZOLYL N'-PHENYL UREA

[75] Inventors: Lewis C. Lappas, Carmel; Leslie J. Lorenz, Indianapolis; James H. Wikel, Greenwood, all of Ind.

[73] Assignee: Eli Lilly and Company, Indianapolis, Ind.

[21] Appl. No.: 10,553

[22] Filed: Feb. 9, 1979

[51] Int. Cl.² .......................................... C07D 277/84
[52] U.S. Cl. .................................... 548/163; 424/270
[58] Field of Search ........................... 260/304 R, 305; 548/163

[56] References Cited

U.S. PATENT DOCUMENTS 4,088,768  5/1978  Paget ..................................... 424/272

Primary Examiner—Donald G. Daus
Assistant Examiner—D. B. Springer
Attorney, Agent, or Firm—James L. Rowe; Arthur R. Whale

[57] ABSTRACT

Crystalline monohydrate (Form III) and anhydrate (Form IV) of N-2-(6-methoxy)benzothiazolyl-N'-phenylurea (frentizole) are stable, have a greater bulk density, are less electrostatic and more freely flowing than previous crystalline forms.

3 Claims, No Drawings

CRYSTALLINE FORMS OF N-2-(6-METHOXY)BENZOTHIAZOLYL N'-PHENYL UREA

BACKGROUND OF THE INVENTION

N-2-(6-Methoxy)benzothiazolyl-N'-phenylurea, generic name frentizole, is presently under clinical investigation as an immune regulant, primarily for the treatment of lupus erythematosis. Early investigations of drug being prepared for clinical trial uncovered the fact that 2-amino-6-methoxybenzothiazole, a mutagenic compound according to the Ames test was present as a contaminant at a concentration of about 1300 ppm. The clinical trial drug was in the form of an anhydrate (Form I) and was prepared by the procedure set forth in U.S. Pat. No. 4,008,768 involving the reaction of 2-amino-6-methoxybenzothiazole and phenylisocyanate followed by recrystallization of the thus-formed urea from acetone. These fiber-like anhydrate (Form 1) crystals, besides carrying a mutagenic impurity, are bulky, electrostatic, and difficult to grind or load into capsules or otherwise formulate.

It is an object of this invention to provide polymorphic crystalline forms of frentizole which are substantially free of mutagenic impurities, have a lower bulk density, are less electrostatic and more free-flowing than the crystalline form provided by the art.

DESCRIPTION OF THE INVENTION

In fullfilment of the above and other objects, this invention provides a monohydrate (Form III) of N-2-(6-methoxy)benzothiazolyl-N'-phenylurea (frentizole) having the following x-ray powder diffraction pattern using copper radiation $\lambda = 1.5418$

| "d" Value (Å) | Intensities ($I/I_1$) |
| --- | --- |
| 15.63 | 74 |
| 6.41 | 29 |
| 6.02 | 60 |
| 5.21 | 10 |
| 5.02 | 7 |
| 4.71 | 12 |
| 4.15 | 21 |
| 4.04 | 3 |
| 3.77 | 10 |
| 3.54 | 40 |
| 3.39 | 100 |
| 3.15 | 3 |
| 2.95 | 2 |
| 2.68 | 9 |
| 2.25 | 7 |
| 2.15 | 2 |
| 2.11 | 2 |
| 1.79 | 2 |
| 1.76 | 2 | and an anhydrate (Form IV) of frentizole having the following x-ray powder diffraction pattern using copper radiation, $\lambda = 1.5418$

| "d" value (Å) | Intensities ($I/I_1$) |
| --- | --- |
| 15.88 | 100 |
| 8.38 | 4 |
| 5.64 | 24 |
| 5.24 | 64 |
| 4.98 | 8 |
| 4.75 | 6 |
| 4.48 | 7 |
| 4.29 | 4 |
| 4.03 | 4 |
| 3.74 | 39 |
| 3.63 | 43 |
| 3.53 | 78 |
| 3.46 | 43 |
| 3.35 | 29 |
| 3.23 | 14 |
| 3.10 | 6 |
| 2.75 | 11 |
| 2.60 | 4 |
| 2.38 | 4 |
| 2.16 | 8 |
| 1.99 | 2 |
| 1.85 | 1 |
| 1.82 | 1 |

The monohydrate of frentizole (Form III) loses water slowly on standing at room temperature in an atmosphere with less than 30 percent relative humidity to form the anhydrate (Form IV). Heating at about 80° C. in vacuo for 4 hours substantially completely converts Form III to Form IV. Recrystallization of the anhydrate from water-acetone or other partially aqueous solvent such as tetrahydrofuran yields monohydrate (Form III) crystals.

Both the anhydrate (Form IV) and monohydrate (Form III) are substantially free from the mutagen, 2-amino-6-methoxybenzothiazole (8 ppm). The new anhydrate (Form IV) is not only stable, but also has a bulk density one-third greater than the original anhydrate (Form I) and is non-electrostatic and flows freely. As such, it is easy to grind and formulate and to fill into capsules.

Preparation of the monohydrate (Form III) and new anhydrate (Form IV) is illustrated in the following examples.

EXAMPLE 1

Two grams of N-2-(6-methoxy)benzothiazolyl-N'-phenylurea(frentizole) Form I were dissolved in 40 ml. of tetrahydrofuran (THF) at room temperature with stirring. 120 ml. of water were added with vigorous stirring. Frentizole monohydrate (Form III) crystallized from the solution and was collected by filtration.

EXAMPLE 2

Fifty-one grams of frentizole were slurried with 1 liter of THF in a 5 l. 3-neck Morton flask equipped with stirrer, condenser and dropping funnel. The slurry was heated to reflux temperature and maintained there for one minute to effect complete solution of the frentizole. 3 l. of water were rapidly added with vigorous stirring. The mixture was stirred at ambient temperature for two hours, during which period of time, frentizole monohydrate (Form III), crystallized. The solution was filtered (30° C. temperature) and the filter cake washed with ether. The crystals were air dried; yield=51.6 g.

Crystalline frentizole monohydrate prepared as above contains from 7-10 ppm of 2-amino-6-methoxybenzothiazole, a decrease from about 1300 ppm in Form I anhydrate crystals.

Frentizole anhydrate (Form IV) produced as above was ground, mixed with polysorbitol mono-oleate, cellulose, sodium carboxymethylcellulose, starch and magnesium stearate and loaded into capsules to provide 25–100 mg of frentizole per capsule.

We claim:

1. Stable crystalline forms of N-2-(6-methoxy)benzothiazolyl-N'-phenylurea of the group consisting of a monohydrate (Form III) having the following x-ray powder diffraction pattern using copper radiation, λ=1.5418

| "d" Value (Å) | Intensities (I/I₁) |
|---|---|
| 15.63 | 74 |
| 6.41 | 29 |
| 6.02 | 60 |
| 5.21 | 10 |
| 5.02 | 7 |
| 4.71 | 12 |
| 4.15 | 21 |
| 4.04 | 3 |
| 3.77 | 10 |
| 3.54 | 40 |
| 3.39 | 100 |
| 3.15 | 3 |
| 2.95 | 2 |
| 2.68 | 9 |
| 2.25 | 7 |
| 2.15 | 2 |
| 2.11 | 2 |
| 1.79 | 2 |
| 1.76 | 2 | and an anhydrate (Form IV) having the following x-ray powder diffraction pattern using copper radiation, λ=1.5418

| "d" value (Å) | Intensities (I/I₁) |
|---|---|
| 15.88 | 100 |
| 8.38 | 4 |
| 5.64 | 24 |
| 5.24 | 64 |
| 4.98 | 8 |
| 4.75 | 6 |
| 4.48 | 7 |
| 4.29 | 4 |
| 4.03 | 4 |
| 3.74 | 39 |
| 3.63 | 43 |
| 3.53 | 78 |
| 3.46 | 43 |
| 3.35 | 29 |
| 3.23 | 14 |
| 3.10 | 6 |
| 2.75 | 11 |
| 2.60 | 4 |
| 2.38 | 4 |
| 2.16 | 8 |
| 1.99 | 2 |
| 1.85 | 1 |
| 1.82 | 1 |

2. A monohydrate (Form III) of N-2-(6-methoxy)-benzothiazolyl-N'-phenylurea according to claim 1 having the following x-ray powder diffraction pattern using copper radiation, λ=1.5418

| "d" Value (Å) | Intensities (I/I₁) |
|---|---|
| 15.63 | 74 |
| 6.41 | 29 |
| 6.02 | 60 |
| 5.21 | 10 |
| 5.02 | 7 |
| 4.71 | 12 |
| 4.15 | 21 |
| 4.04 | 3 |
| 3.77 | 10 |
| 3.54 | 40 |
| 3.39 | 100 |
| 3.15 | 3 |
| 2.95 | 2 |
| 2.68 | 9 |
| 2.25 | 7 |
| 2.15 | 2 |
| 2.11 | 2 |
| 1.79 | 2 |
| 1.76 | 2 |

3. An anhydrate (Form IV) of N-2-(6-methoxy)-benzothiazolyl-N'-phenyl urea according to claim 1 having the following x-ray powder diffraction pattern using copper radiation, λ=1.5418

| "d" Value (Å) | Intensities (I/I₁) |
|---|---|
| 15.88 | 100 |
| 8.38 | 4 |
| 5.64 | 24 |
| 5.24 | 64 |
| 4.98 | 8 |
| 4.75 | 6 |
| 4.48 | 7 |
| 4.29 | 4 |
| 4.03 | 4 |
| 3.74 | 39 |
| 3.63 | 43 |
| 3.53 | 78 |
| 3.46 | 43 |
| 3.35 | 29 |
| 3.23 | 14 |
| 3.10 | 6 |
| 2.75 | 11 |
| 2.60 | 4 |
| 2.38 | 4 |
| 2.16 | 8 |
| 1.99 | 2 |
| 1.85 | 1 |
| 1.82 | 1 |

* * * * *